United States Patent [19]

Böhm et al.

[11] Patent Number: 5,223,643
[45] Date of Patent: Jun. 29, 1993

[54] PROCESS FOR THE PREPARATION OF 1,1-DIFLUOROALKANESULPHENYL CHLORIDES

[75] Inventors: Stefan Böhm; Albrecht Marhold, both of Leverkusen; Dietmar Bielefeldt, Ratingen, all of Fed. Rep. of Germany

[73] Assignee: Bayer Aktiengesellschaft, Leverkusen, Fed. Rep. of Germany

[21] Appl. No.: 789,214

[22] Filed: Nov. 7, 1991

[30] Foreign Application Priority Data

Nov. 16, 1990 [DE]  Fed. Rep. of Germany ....... 4036515

[51] Int. Cl.$^5$ .......................................... C07C 323/03
[52] U.S. Cl. ...................................... 562/821; 568/56
[58] Field of Search ........................... 562/821; 568/56

[56] References Cited

U.S. PATENT DOCUMENTS 3,839,403  10/1974  Phillips .............................. 562/821

OTHER PUBLICATIONS

March, *Advanced Organic Chemistry*, 3rd ed., p. 687 (1985).
Harris et al., *JACS 83*, pp. 840–845 (1961).
Dear et al., *J. Chem. Eng. Data, 14*, pp. 493–497 (1969).

Primary Examiner—Paul J. Killos
Assistant Examiner—B. Frazier
Attorney, Agent, or Firm—Sprung Horn Kramer & Woods

[57] ABSTRACT

The present invention relates to a multi-step process for the preparation of 1,1-difluoroalkanesulphenyl chlorides of the general formula (I):

$$R-CH_2-CF_2-S-Cl$$

The process comprises the following steps:
(1) $R^1-SH + R-CH=CF_2 \rightarrow R^1-S-CF_2-CH_2-R$
(2) $R^1-S-CF_2-CH_2-R + \text{chlorine agent} \rightarrow Cl-S-CF_2-CH_2-R$ Step (1) is carried out in a base at 0° C.–250° C., optionally in the presence of a solvent and/or a phase transfer catalyst. Step (2) is carried out at −78° C.–100° C., optionally in a solvent and optionally after the product of step (1) has been isolated. The final products are intermediates for organic syntheses.

10 Claims, No Drawings

PROCESS FOR THE PREPARATION OF 1,1-DIFLUOROALKANESULPHENYL CHLORIDES

The present invention relates to a new process for the preparation of 1,1-difluoroalkanesulphenyl chlorides, which can be used as intermediates for organic syntheses.

It has been found that the 1,1-difluoroalkanesulphenyl chlorides of the general formula (I)

$$R-CH_2-CF_2-S-Cl \quad (I)$$

in which
R represents hydrogen or alkyl, are obtained when
a) mercaptans of the general formula (II)

$$R^1-SH \quad (II)$$

in which
$R^1$ represents t-butyl or the benzyl group

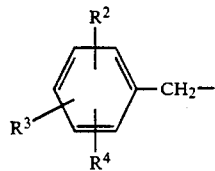

in which
$R^2$, $R^3$ and $R^4$ are identical or different and represent hydrogen, halogen or alkyl,
are reacted with the vinylidene fluorides of the general formula (III)

$$R-CH=CF_2 \quad (III)$$

in which
R has the abovementioned meanings,
in the presence of a base and if appropriate in the presence of a solvent and if appropriate in the presence of a phase transfer catalyst, at temperatures between 0° and 250° C. and
b) the resulting compounds of the general formula (IV)

$$R^1-S-CF_2-CH_2-R \quad (IV)$$

in which
R and $R^1$ have the abovementioned meanings,
if appropriate after their isolation or if appropriate after isolation of the mixtures of the compounds of the general formula (IV) formed under a) and the by-products of the general formula (V)

$$R^1-S-CF=CH-R \quad (V)$$

in which
R and $R^1$ have the abovementioned meanings,
are reacted with a chlorinating agent, if appropriate in the presence of a solvent, at temperatures between −78° C. and 100° C. and the resulting 1,1-difluoroalkanesulphenyl chlorides of the general formula (I) are isolated.

The process according to the invention enables the preparation of the 1,1-difluoroalkanesulphenyl chlorides of the general formula (I) in good yield and purity. It is also particularly suitable as an industrial process for the preparation of relatively large amounts of these compounds. The ability to be able to carry out the process smoothly was not to be expected with knowledge of the prior art. Admittedly the nucleophilic addition of certain alcohols to vinylidene fluoride is known [R. E. A. Dear and E. E. Gilbert, J. Chem. Eng. Data 14, 493 to 497 (1969)], but the experiences to date with mercapto compounds allowed the conclusion that a smooth reaction with mercapto compounds would not take place.

In the general formulae, alkyl denotes straight-chain or branched alkyl preferably having 1 to 8, in particular 1 to 6 and particularly preferably 1 to 4 carbon atoms. The following may be mentioned as preferred: methyl, ethyl, n.- and i.-propyl and n.-, i.-, sec.- and t.-butyl. Methyl and ethyl may be particularly emphasised, in particular methyl.

Halogen in the general formulae denotes fluorine, chlorine, bromine and iodine, preferably fluorine, chlorine and bromine, particularly preferably fluorine and chlorine and very particularly preferably chlorine.

R preferably represents hydrogen or methyl, particularly preferably hydrogen.

The benzyl group (compare definition of $R^1$) can carry 1 to 3, preferably 1 or 2, of the substituents mentioned. 4-methylbenzyl and 4-chlorobenzyl may be mentioned as preferred. The unsubstituted benzyl group ($R^2$, $R^3$ and $R^4$ represent hydrogen) is particularly preferred.

In a particularly preferred embodiment of the invention, R represents hydrogen and R: represents the benzyl group, $R^2$, $R^3$ and $R^4$ denoting hydrogen.

The process according to the invention is very particularly preferably employed for the preparation of 1,1-difluoroethanesulphenyl chloride (compound of the formula (I) where R=hydrogen).

The process according to the invention is intended to be illustrated by the following (non-stoichiometric) equation:

Step (a)

$$R_1-SH + R-CH=CF_2 \xrightarrow{\text{Base}}$$
$$(II) \quad\quad (III)$$

$$R^1-S-CF_2-CH_2-R + R^1-S-CF=CH-R$$
$$(IV) \quad\quad\quad\quad (V)$$

Step (b)

$$R^1-S-CF_2-CH_2-R \xrightarrow{\text{chlorinating agent}}$$
$$(IV)$$

$$R-CH_2-CF_2-S-Cl + R^1-Cl$$
$$(I)$$

Process step (a) according to the invention is carried out in the presence of a base. Inorganic bases, such as alkali metal hydroxides and alkaline earth metal hydroxides, such as sodium hydroxide and/or potassium hydroxide or calcium hydroxide and organic bases, such as trialkylamines, for example triethylamine, amidine bases, for example diazabicycloundecene or diazabicyclononene can be used for this. Basic ion exchangers can also be employed. Alkali metal hydroxides (sodium hydroxide and/or potassium hydroxide) are preferably employed, aqueous solutions preferably being used.

The base is employed in at least a 1 molar amount, preferably in a 1 to 3 molar and particularly preferably in a 1 to 2 molar amount [relative to the compound of the formula (II)].

Process step (a) according to the invention can be carried out without solvent or, preferably, in the presence of a solvent. Solvents which can be employed are all organic solvents which are inert in the reaction, preferably solvents which are not or only slightly watermiscible. Preferred solvents which may be mentioned and which may be used individually or alternatively in mixtures are:

aromatic hydrocarbons, such as benzene, toluene and xylenes, aliphatic and cycloaliphatic hydrocarbons, such as petroleum ether and cyclohexane, ethers, such as di-n-butyl ether or methyl t-butyl ether. Toluene is particularly preferably used.

Process step (a) according to the invention is preferably carried out in the presence of a phase transfer catalyst, it being possible to use all customary phase transfer catalysts. Quaternary ammonium salts (in particular tetra-$C_2$-$C_4$-alkyl and benzylammonium chlorides), such as tetra-n-butylammonium chloride and particularly preferably triethylbenzylammonium chloride (TEBA) are preferably employed.

The phase transfer catalysts are employed in amounts of preferably 1 to 50, in particular 5 to 20 g, per liter of the solvent used.

Process step (a) according to the invention is carried out at temperatures between 0° and 250° C., preferably between 50° and 200° C. and particularly preferably between 80° and 120° C.

1 to 5 mol, preferably 1 to 2.5 and particularly preferably 1 to 1.5 mol, of the vinylidene fluoride (III) are employed per mole of mercaptan (II) in process step (a) according to the invention.

The compounds of the formula (II) are reacted with the compounds of the formula (III) in a pressure vessel and the reaction is carried out at pressures preferably between 1 and 50 bar, in particular between 5 and 30 bar, the respective pressure resulting through the addition (pumping in) of the vinylidene fluorides of the formula (III) and through the temperature control.

The reaction products obtained according to process step (a) are isolated by the customary methods, preferably by aqueous extraction, and can be purified by distillation. The compounds of the formula (IV) can also be removed by distillation from the compounds of the formula (V) formed as by-products. For reprocessing in process step (b), however, such a removal of the by-products of the formula (V) is not necessary, as they do not interfere in the further reaction.

In a preferred embodiment of process step (a), the compounds of the formula (II) are dissolved in a solvent in a pressure vessel and treated with the aqueous solution of the base and optionally with the phase transfer catalyst. The compounds of the formula (III) are added (pumped in) at elevated temperature in the course of 1 to 18 hours, a corresponding pressure being built up. After the reaction is complete, the phases are separated (optionally with the addition of hydrochloric acid) and the desired compounds are isolated from the organic phase.

Process step (b) according to the invention can be carried out using all chlorinating agents suitable for the chlorolysis. Suitable and preferred chlorinating agents which may be mentioned are sulphuryl chloride, N-chlorosuccinimide and very particularly preferably chlorine.

The chlorolysis (b) can be carried out in the presence of solvents or, preferably, without the addition of solvents. Solvents which can be employed are all organic solvents which are inert in the chlorination reaction. Halogenated (fluorine- and/or chlorine-substituted) hydrocarbons, such as carbon tetrachloride and methylene chloride and Freons or Frigens are preferably used.

The chlorination reaction (b) is carried out at temperatures between −78° and 100° C., preferably between −30° and 25° C. and particularly preferably between −20° and 0° C.

Preferably 1 to 5 mol, particularly preferably 1 to 3 mol, of the chlorinating agent are employed per mole of the compounds of the formula (IV) in the chlorination reaction (b).

The desired final products of the formula (I) are isolated from the reaction mixture by distillation and optionally further purified by distillation.

In a preferred embodiment of process step (b), the mixture obtained from the compounds of the formulae (IV) and (V) in step (a) is treated with chlorine at the temperatures indicated and the progress of the reaction is monitored analytically by gas chromatography. As soon as compound of the formula (IV) can no longer be detected, the desired product of the formula (I) is removed by distillation under a slight vacuum.

The compounds of the general formula (I) obtainable according to the invention are useful precursors and intermediates for organic syntheses, for example for the preparation of insecticidal phosphoric acid esters (compare DE-A 3,903,409). Thus, for example, the 1,1-difluoroethanesulphenyl chloride obtainable according to the invention can be reacted with S-s-butyl O,O-diethyl thiophosphite in dichloromethane as a solvent to give the insecticidally active O-ethyl S-s-butyl S-(1,1-difluoroethyl) dithiophosphate (b.p. 75° C./1.3 mbar). This phosphoric acid ester can be formulated in a customary manner to give a plant protection agent which can be employed as an insecticide in a customary manner.

The following examples are intended to illustrate the process according to the invention. Where not stated otherwise, all % data in the present text relate to percentages by weight.

EXAMPLE 1a [Step (a)]

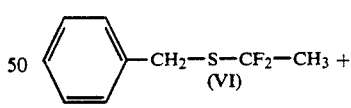
(VI)

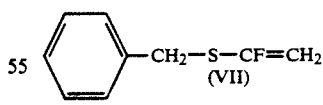
(VII)

420 g (3.4 mol) of benzyl mercaptan are dissolved in 600 ml of toluene at about 20° C. in an autoclave and treated with 600 ml of aqueous 45% strength sodium hydroxide solution and 10 g of triethylbenzylammonium chloride (TEBA). 320 g (5 mol) of vinylidene fluoride are pumped in at 100° C. in the course of 12 hours, the pressure rising from 5 to 25 bar. The mixture is then stirred at 100° C. for 12 hours. After cooling and depressurising, the mixture is poured into 2 liters of 10% strength aqueous hydrochloric acid, the phases are separated and the aqueous phase is extracted with toluene.

The combined organic phases are washed with NaCl solution, dried using MgSO₄ and fractionated in vacuo.

460 g (72% conversion) of a 2:1 mixture of benzyl 1,1-difluoroethyl sulphide (VI) and benzyl 1-fluorovinyl sulphide (VII) having a boiling range of 72° to 75° C. at 2 mbar are obtained.

The ¹H-NMR spectrum of (VI) (200 MHz, CDCl₃, TMS internal) shows characteristic bands at 7.28 ppm (m, 5 H, —Ph), 4.05 ppm (s, 2 H, —CH₂—) and 1.88 ppm (t, 3 H, —CH₃—, J=16.7 Hz).

The ¹⁹F-NMR spectrum of (VI) (75.4 MHz, CDCl₃, CF₃COOH ext.) shows a quartet at 11.5 ppm (J=16.7 Hz).

The ¹H-NMR spectrum of (VII) (200 MHz, CDCl₃, TMS internal) shows characteristic bands at 7.28 ppm (m, 5 H, —Ph), 4.90 ppm (dd, 1 H, =CH, $J_{H,H}$=3 Hz, $J_{H,F}$=12 Hz), 4.62 ppm (dd, 1 H, =CH, $J_{H,H}$=3 Hz, $J_{H,F}$=43 Hz), 3.93 ppm (s, 2 H, —CH₂—).

The ¹⁰F-NMR spectrum of (VII) (75.4 MHz, CDCl₃, CF₃COOH ext.) shows a doublet of doublets at −2.0 ppm ($J_{H,F}$=12 Hz and 43 Hz).

EXAMPLE 1b [Step (b)]

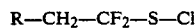    (VIII)

326 g (1.14 mol of VI/0.66 mol of VII) of the sulphide mixture from Example 1a are treated with excess chlorine (177 g, 2.5 mol) at −15° C. until (VI) is no longer present according to the gas chromatogram. The product is then distilled off by applying a slight vacuum. 158 g (90%) of 1,1-difluoroethanesulphenyl chloride (VIII) are obtained having a boiling point of 62° C. at normal pressure and a purity of 90% (GC).

The ¹H-NMR spectrum of (VIII) (200 MHz, CDCl₃, TMS internal) shows characteristic bands at 2.04 ppm (t, —CH₃, $J_{H,F}$=16.5 Hz).

The ¹⁰F-NMR spectrum of (VIII) (75.4 MHz, CDCl₃, CF₃COOH ext.) shows characteristic bands at 6.2 ppm (q, $J_{H,F}$=16.5 Hz).

We claim:

1. Process for the preparation of 1,1-difluoroalkanesulphenyl chlorides of the general formula (I)

in which
R¹ represents hydrogen or alkyl, characterized in that
a) mercaptans of the general formula (II)

    (II)

in which
R¹ represents t-butyl or the benzyl group

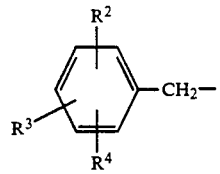

in which
R², R³ and R⁴ are identical or different and represent hydrogen, halogen or alkyl, are reacted with the vinylidene fluorides of the general formula (III)

R—CH=CF₂    (III)

in which
R has the above-mentioned meanings,
in the presence of a base and optionally in the presence of a solvent and optionally in the presence of a phase transfer catalyst, at temperatures between 0° and 250° C., wherein the base is employed in at least a 1 molar amount and the base is selected form the group consisting of alkali metal hydroxides, alkaline earth metal hydroxides, trialkylamines, and amidines, and b) the resulting compounds of the general formula (IV)

R¹—S—CF₂—CH₂—R    (IV)

in which
R and R¹ have the above-mentioned meanings, optionally after their isolation or optionally after isolation of the mixtures of the compounds of the general formula (IV) formed under a) and the by-products of the general formula (V)

R¹—S—CF=CH—R    (V)

in which
R and R¹ have the above-mentioned meanings, are reacted with a chlorinating agent, optionally in the presence of a solvent, at temperatures between −78° C. and 100° C. and the resulting 1,1-difluoroalkanesulphenyl chlorides of the general formula (I) are isolated.

2. Process according to claim 1, where R represents hydrogen or alkyl.

3. Process according to claim 1, where R represents hydrogen.

4. Process according to claim 1, where R¹ represents the benzyl group and R², R³ and R⁴ denote hydrogen.

5. Process according to claim 1, where step (a) is carried out in the presence of toluene.

6. Process according to claim 1, where sodium hydroxide is employed as the base in step (a).

7. Process according to claim 1, where triethylbenzylammoniumchloride is used in step (a) as the phase transfer catalyst.

8. Process according to claim 1, where the mixture of the compounds of the formulae (IV) and (V) obtained in step (a) is employed in step (b).

9. Process according to claim 1, where step (b) is carried out without solvent.

10. Process according to claim 1, where chlorine is employed as the chlorinating agent in step (b).

* * * * *